United States Patent [19]

Baker, Jr.

[11] Patent Number: 4,762,136
[45] Date of Patent: * Aug. 9, 1988

[54] LOW POLARIZATION PACING ELECTRODES FOR CAPTURE VERIFICATION

[75] Inventor: Ross G. Baker, Jr., Houston, Tex.

[73] Assignee: Intermedics, Inc., Angleton, Tex.

[*] Notice: The portion of the term of this patent subsequent to Jul. 14, 2004 has been disclaimed.

[21] Appl. No.: 16,379

[22] Filed: Feb. 19, 1987

[51] Int. Cl.$^4$ .............................................. A61N 1/05
[52] U.S. Cl. .................................. 128/786; 128/785; 128/419 P
[58] Field of Search ............................. 128/784–786, 128/419, 642

[56] References Cited

U.S. PATENT DOCUMENTS

| | | | |
|---|---|---|---|
| 3,735,766 | 5/1973 | Bowers et al. | 128/419 p |
| 4,407,302 | 10/1983 | Hirshorn et al. | 128/419 P |
| 4,440,178 | 4/1984 | Bussard et al. | 128/419 P |
| 4,502,492 | 3/1985 | Bornzin | 128/785 |
| 4,573,481 | 3/1986 | Bullare | 128/784 |
| 4,677,989 | 7/1987 | Robblee | 128/784 |
| 4,679,572 | 7/1987 | Baker, Jr. | 128/786 |

OTHER PUBLICATIONS

Robblee et al, "Activated Ir: An Electrode . . . ", J. Electrochem. Soc., pp. 731–733, vol. 130, No. 3, Mar. 1983.

Primary Examiner—Lee S. Cohen
Attorney, Agent, or Firm—Leitner, Greene & Christensen

[57] ABSTRACT

An electrode for use in cardiac pacing has a substrate composed of a material conventionally employed for pacing electrodes, and a surface layer or film of iridium oxide overlying the substrate. For use as a stimulating cathodic electrode and a sensing electrode, the iridium oxide layer is arranged to be in cardiac tissue stimulating relationship when the electrode is in proper position with respect to the patient's heart. The electrode impresses electrical stimuli on the excitable myocardial tissue, and at the completion of each stimulus, the electrode is capable of abruptly sensing, within an interval less than 100 ms thereafter, the electrical activity of the heart in response to the stimulus to verify capture. The surface of the electrode may be provided with recesses to which the iridium oxide layer may be confined. An iridium oxide layer may be provided on both the cathode and the anode for efficient transduction at the electrode-electrolyte interface formed by the surface of the iridium oxide layer and the surrounding body fluid and tissue.

10 Claims, 2 Drawing Sheets

LOW POLARIZATION PACING ELECTRODES FOR CAPTURE VERIFICATION

BACKGROUND OF THE INVENTION

The present invention relates generally to artificial cardiac pacing, and more particularly to improved pacing electrodes for stimulating and sensing electrical activity of the heart, and to pacing lead assemblies incorporating such electrodes.

The sinoatrial (S-A) node of the normal mammalian heart acts as the natural pacemaker by which rhythmic electrical excitation is developed and propagated to the atria. In response, the atrial chambers contract, pumping blood into the ventricles. The excitation is propagated through the atrioventricular (A-V) node, which imposes a delay, and then via the conduction system consisting of the bundle of His and Purkinge fibers to the ventricular myocardium, causing contraction and the pumping of blood from the ventricles. Disruption of this natural pacing/propagation system occurs as a result of aging and disease.

Where the human patient has an abnormally slow or abnormally rapid heart rate, or the rate is irregular, it is customary for the cardiologist to prescribe implantation of an artificial cardiac pacemaker selected according to the specific patient's needs. In its simplest form, the cardiac pacemaker consists of a pulse generator with a battery pack, and a lead assembly. The lead assembly includes a pacing electrode to be positioned in stimulating relationship to excitable myocardial tissue, and an insulated electrical coil interconnecting the pulse generator and the pacing electrode to deliver the electrical pulses to the electrode to stimulate the tissue. The electrical circuit is completed via a second electrode (the indifferent or reference electrode), which is connected to a point of reference potential for the cardiac pacemaker, and through the body tissue and fluids. The stimulating electrode may also be used as a sensing electrode by coupling to a detection circuit to sense the electrical activity of the heart. The entire lead/electrode assembly is often referred to simply as the "lead".

In the instant specification, the pacing electrode is sometimes referred to as the stimulating cathodic electrode, the stimulating electrode, or the cathode, and the indifferent electrode is sometimes referred to as the reference electrode, the anodic electrode, or the anode. It will be understood, however, that electrical activity takes place at each electrode during pacing, and that the coupling may be such that each electrode acts, at different times, as cathode or anode.

The lead of choice for use with the cardiac pacemaker is an endocardial catheter, which is readily inserted transvenously to introduce the stimulating electrode into the cardiac chamber to be paced. In contrast, an epicardial lead requires thoracic surgery to affix the electrode to the surface of the heart. Various forms of active or passive fixation may be employed to maintain the stimulating electrode in proper position relative to the excitable heart tissue, such as sutures (epicardial), a corkscrew or flexible barbs, hooks or tines fastened to the lead in proximity to the electrode.

The cardiac pacemaker may employ unipolar or bipolar stimulation, depending on the preference of the physician and the needs of the patient. For unipolar stimulation, the anode is located remote from the heart, and typically comprises the metal case or portion thereof that houses the batteries, pulse generator and other electronic circuitry of the pacemaker. For bipolar stimulation, the two electrodes are in close proximity, typically with the cathode being at the tip and the anode spaced slightly back from the tip as a ring electrode on the lead.

The cardiac pacemaker may operate in any of several different response modes, including asynchronous, or fixed rate; inhibited, in which stimuli are generated in the absence of specified normal cardiac activity; or triggered, in which the stimuli are delivered in response to specified cardiac activity. In each of these modes, output pulses from the pulse generator are delivered via the lead for electrical stimulation of excitable myocardial tissue at or near the site of the cathode, thereby producing the desired rhythmic contractions of the affected chamber. Since stimulation is attributable to current density, small area stimulating electrodes will suffice. The current required to produce a given current density decreases in direct proportion to the active area of the electrode. Small area cathodic electrodes therefore serve to prolong battery life, and increase the interval between required surgical replacements.

In essence, stimulation requires that the electric field be of sufficient field strength and current density to initiate contraction of excitable myocardial tissue at the cathode site. The minimum electrical impulse necessary to achieve this is referred to as the stimulation threshold. The greater the efficiency of the cathode in impressing the electric field on the tissue, the smaller the amplitude and/or duration of (and the energy contained in) the pacing pulse required to achieve the stimulation threshold. Accordingly, highly efficient, low threshold electrodes conserve energy and prolong battery life. Because greater electrode efficiency reduces energy required for stimulation, it may be a factor in reducing injury to tissue at the stimulation site.

Cardiac pacing may be achieved with anodal rather than cathodal stimulation, but the stimulation threshold is higher because the polarizing force of the stimulating electric field on ions at the surface of membranes of the excitable myocardial cells reduces transmembrane potential on the side of each affected cell furthest from the anode, at a point of relatively lower field intensity; in contrast to reduction of the potential at the near side with cathodal stimulation.

Regardless of the type of pacemaker implanted, from the simple fixed rate device to the complex dual chamber pacing/sensing devices and the latest physiologic pacers, it is important to ascertain that the stimulus is having the desired effect. Pulse generation which causes contraction of the selected chamber is termed "capture", and the method of determining that the pacer stimuli are achieving capture is called "capture verification". Capture verification techniques are based on detecting the potential evoked when the heart is captured. If there is no capture, there is no evoked potential, and the amplitude and/or duration of the stimulating pulse must then be adjusted to assure consistent capture. It follows that each time the heart is paced, the cardiac electrical activity may be monitored to detect the presence of the evoked potential and thereby verify capture.

In practice, however, capture verification is fraught with problems, one of the more significant being of a signal-to-noise nature in which the signal sought to be detected is masked by after-potentials attributable to electrode polarization. After the stimulating pulse is delivered, the electrode must "settle down" to allow detection of the evoked potential indicative of capture. This requires a suitable period of delay, which itself precludes the desired detection. Accordingly, some capture verification techniques seek to filter the signal from the masking after-potential, necessitating additional circuitry and space.

SUMMARY OF THE INVENTION

In copending U.S. patent application Ser. No. 838,607, filed Mar. 11, 1986, now U.S. Pat. No. 4,679,572, entitled "Low Threshold Cardiac Pacing Electrodes" (the "copending Ser. No. 838,607 application"), and assigned to the same assignee as this application, I disclose a stimulating electrode for cardiac pacing or other cardiac stimulation functions, in which an iridium oxide layer is formed on the electrode surface to provide a considerable reduction in the stimulation threshold as compared to electrodes and electrode materials and compositions previously employed in the cardiac pacing field. The iridium oxide coating provides advantages in cardiac electrodes used as either cathodes or anodes. Among other advantages of such electrodes, the lower threshold may be a factor in reducing injury to myocardial tissue at the stimulation site; and iridium oxide appears to possess greater physical integrity and superior charge transfer capability per unit area than materials heretofore commonly employed for cardiac stimulation applications, including specialized coatings such as platinum black.

As noted in the copending Ser. No. 838,607 application, iridium oxide electrodes had previously been used in various other applications, such as in electrochromic displays (e.g., see Dautremont-Smith et al., "Electrochromic Cells with Iridium Oxide Display Electrodes", *Solid State Ionics* 2 (1981) pp. 13–18); and including certain medical applications, such as for measuring tissue impedances (e.g., see Gielen et al., "Comparison of electrode impedances of Pt, PtIr (10% Ir) and Ir-AIROF electrodes used in electrophysiological experiments", *Medical and Biological Engineering & Computing*, January 1982, pp. 77–83); for measuring acidity in the upper gastro-intestinal tract (e.g., see Papeschi et al., "The iridium/iridium oxide electrode for in vivo measurement of oesophagael and gastric pH", *Journal of Medical Engineering and Technology*, Vol. 8, No. 5, September–October 1984, pp. 221–223); and for measuring acidity changes in the blood (e.g., see Papeschi et al., "An iridium/iridium oxide electrode for in vivo monitoring of blood pH changes", *Journal of Medical engineering and Technology*, Vol. 5, No. 2, March 1981, pp. 86–88, and Cammilli et al., "Preliminary Experience with the pH-triggered Pacemaker", *PACE*, Vol. 1, October–December 1978, pp. 448–457). In the Cammilli et al. publication, the authors reported on the use of an iridium oxide electrode for continuous in vivo detection of variations of mixed venous blood pH. According to the article, a rapid decrease of blood pH was utilized as a measure of variation of the patient's metabolic rate and employed to produce an appropriate variation in the stimulation rate for physiological pacing.

Such reports neither teach nor suggest using an iridium oxide electrode for stimulating or sensing electrical activity of the heart. Indeed, in the medical applications of iridium oxide electrodes previously reported, any stray electrical signals would have been deemed as interfering with and undesirable to the purpose for which the electrodes were being used.

Although iridium oxide electrodes have been used more recently in electrophysiological experiments, such as for neuroelectrical experimentation with brain activity in small animals, the proposal for such use was attributable to an absolute requirement for extremely fine electrode wires, with active surface areas on the order of 20 square microns. It had been found that even platinum electrodes of such tiny size disintegrated on the passage therethrough of relatively low levels of current. It was found that an iridium oxide coating was capable of withstanding the necessary current without significant deterioration. In contrast to the relatively tiny surface areas of concern in these physiological experiments, electrodes for the stimulation of excitable cardiac tissue, or for the detection of cardiac electrical activity, require considerably greater surface areas.

The copending Ser. No. 838,607 application notes finding that iridium oxide possesses an extraordinary capability to perform as a charge flow transducer between media exhibiting different charge flow mechanisms, and, despite its relatively inferior characteristics as an electrical conductor compared to conventional pacing electrode materials, that certain properties of iridium oxide make it particularly effective for application in electrodes for stimulating and/or sensing electrical activity of the heart. This appears to arise, in part, from the two basic mechanisms for current flow across a pacing electrode. One is the purely capacitive mechanism by which electron flow away from the cathode causes electrical charges in the solution at the electrode-electrolyte interface to orient themselves such that a displacement current occurs through the electrolyte, i.e., because the electrolyte is an ionic medium, the slight displacement of the ions in reorientation creates a charge flow. When the electrical potential across the electrode-electrolyte interface is sufficiently large, chemical reactions begin to occur and current flows. At that point, the mechanism is no longer capacitive. With conventional electrode materials, the chemical reactions are substantially irreversible.

Iridium oxide demonstrates a capacity to readily accept electrons out of an electrolytic solution, and thus can operate as a highly efficient transducer between an electron flow conductor—such as a metal electrode—and an ionic flow conductor—such as the saline fluid of the body.

Iridium oxide may be deposited as a relatively thick porous layer on a metal substrate for use as a pacing electrode, in both stimulating and sensing applications. The porous structure accommodates water from the body saline. In a typical reaction involving a conventional electrode, a negative potential on the electrode repels electrons, and hydrogen is released from the water in the process. In contrast, with an iridium oxide layer relatively tiny potential differences across the electrode-electrolyte interface are effective to produce the reactions and consequent current flow, while the pores trap the reaction products that would otherwise diffuse away and might injure tissue in the vicinity of the stimulation site. More importantly, with the iridium oxide electrode the reactions are reversible upon reversal of the voltage.

A capacitive effect occurs with an iridium oxide coated electrode, but to a considerably lesser extent than that occurring, for example, with a platinum electrode. Rather, the interface across the iridium oxide surface appears to be primarily resistive. Thus, an iridium oxide coated pacing electrode exhibits lower polarization than is observed with conventional pacing electrodes; which is to say that the voltage buildup at the interface is smaller for a given charge flow through the iridium oxide electrode.

The present invention takes advantage of the low polarization and related attributes of an iridium oxide coated pacing electrode. The low polarization and resultant relatively small voltage buildup at the interface not only make available more energy from each pacing pulse for tissue stimulation, but importantly allow the detection of cardiac electrical activity virtually immediately after stimulation. Therefore, an iridium oxide coated electrode may be used for both stimulation and sensing of cardiac activity to effect low threshold capture and, as a result of the electrode's rapid recovery from the after-potential which follows delivery of the stimulus, to provide virtually instantaneous verification of capture. It is noteworthy that such capture verification is achieved without the need for special filter circuitry or other apparatus beyond the usual detection circuit.

Although the reasons for the highly efficient behavior of iridium oxide as a charge flow transducer between media exhibiting different charge flow mechanisms are not fully understood, it further appears to be attributable to the numerous oxidation states within a film of the material. These oxidation states seem to be relatively stable, with low activation energies, and, therefore, the layer tends to perform more as a resistor than a capacitor. The result is that current flow is facilitated, but without the buildup of residual voltages. The primarily resistive nature of the electrode-electrolyte interface enables rapid dissipation of any after-potential, in contrast to the usual resistive-capacitive mechanism encountered with conventional pacing electrodes by which the passage of current causes a capacitive buildup of voltage and an R-C decay. Whatever may be the reasons for this advantageous behavior of the iridium oxide film, the virtual absence of residual voltages serves to eliminate the masking delay that inevitably follows cardiac stimulation with conventional pacing electrodes, and permits reliable sensing of the evoked potential attributable to capture.

Accordingly, it is a principal object of the present invention to provide improvements in capture verification for cardiac pacing.

In a preferred embodiment of the invention, an iridium oxide layer is provided on the exposed surface of a pacing electrode adapted to be positioned in electrically stimulating and sensing relationship with the excitable myocardial tissue at a pre-selected stimulation site. The underlying substrate of the electrode may be composed of any conventional material for pacing electrode applications, such as titanium, and is preferably but not necessarily a porous structure. The substrate surface may be grooved, dimpled or rippled to provide recesses to which the iridium oxide film may be confined to remove those regions of highest current density from direct contact with the tissue.

The iridium oxide coated electrode is electrically connected to a conductive coil within the lead, which itself is coupled both to the output circuit of the pulse generator and to the detection circuit. The latter is connected at all times but the system logic ignores any input during the refractory period. The pulse generator delivers a pulse to the heart through the stimulating and indifferent electrodes via a coupling capacitor which is then actively discharged by reversal of current flow. The sense amplifier is disconnected during pacing and until the active discharge time elapses.

Further objects of the invention are to provide a pacing electrode for both stimulating and sensing electrical activity of the heart, with low polarization and reduced residual voltage to preclude masking of the evoked potential following capture and, thereby, to enable relatively rapid sensing of the evoked potential for capture verification; and to provide improved methods for artificial pacing and capture verification.

BRIEF DESCRIPTION OF THE DRAWINGS

The above and still further objects, features, aspects and advantages of the present invention will become apparent to those of ordinary skill in the field to which the invention pertains from a consideration of the following detailed description of certain preferred embodiments, taken in conjunction with the accompanying drawings, in which.

DETAILED DESCRIPTION OF THE PREFERRED EMBODIMENTS

Figure 1:
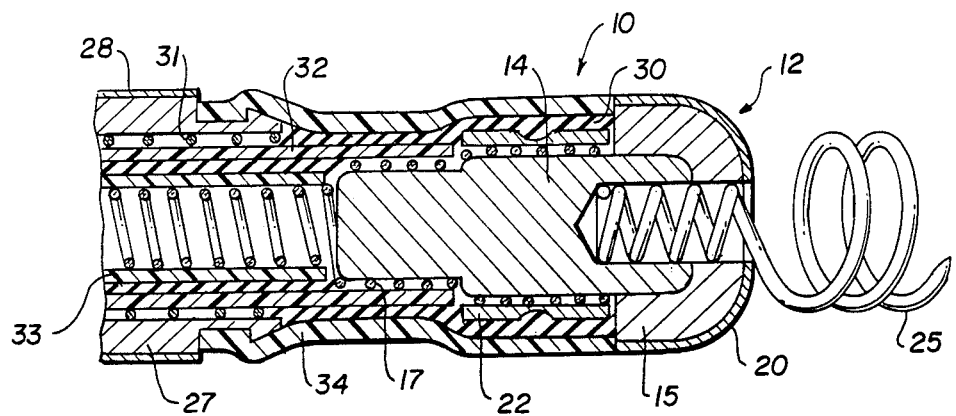
FIG. 1 is a simplified cross-sectional view of a pacing electrode assembly according to the invention, taken along the axis of the configuration, which is circular in transverse cross-section.
Figure 2:
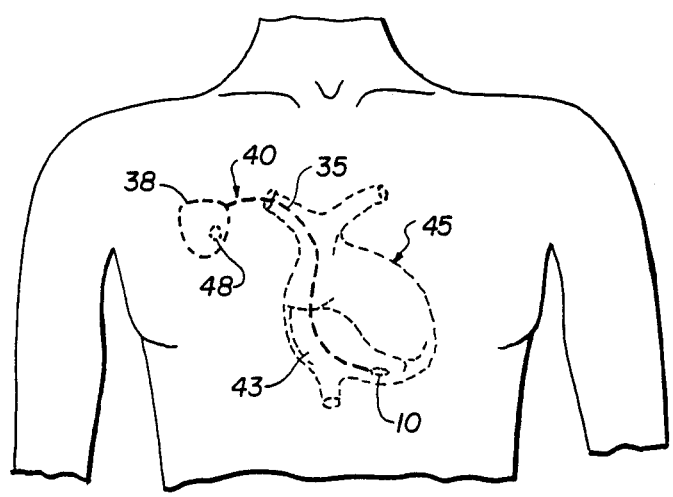
FIG. 2 is a simplified representation of an alternative embodiment of a pacing electrode assembly as part of a lead assembly arranged for unipolar stimulation, in a cardiac pacemaker implanted in the body.

Referring now to FIG. 1, electrode assembly 10 is part of and located at the distal end of a pacing lead assembly (to be described more fully in connection with FIG. 2). The proximal end of the lead assembly is conventionally arranged for connection to the pulse generator of an implantable cardiac pacemaker. The electrode assembly shown in FIG. 1 is a simplified depiction since there is no need to illustrate those details of electrode structure which are well known.

Assembly 10 is configured for endocardial positioning, in which tip electrode (cathode) 12 is adapted to be placed in electrically stimulating relationship with excitable cardiac tissue within a selected chamber of the heart. Substrate 15 of tip 12, and integral stem 14, are composed of any conventional electrode materials, such as platinum, platinumiridium alloy, iridium, tantalum, or titanium, by way of example; and preferably, titanium. A coil 17 of electrically conductive wire within the lead assembly is maintained in solid electrical contact with tip 12 by means of a metal sleeve 22 crimping the coil against the stem. A corkscrew 25 may be affixed to the electrode assembly in a conventional manner to provide active fixation of the stimulating electrode to the myocardium after the electrode has been positioned properly in the selected chamber.

The surface of the cathodic tip electrode 12 is coated with a film or layer 20 of iridium oxide, which may be an AIROF (anodized iridium oxide film), SIROF (sputtered iridium oxide film), TIROF (thermal iridium oxide film), or a layer formed in any other suitable manner. The particular process by which the iridium oxide film or layer is provided on the substrate forms no part of the present invention. The iridium oxide layer may have a thickness of approximately 200 nanometers, although any layer thickness exceeding about 100 nanometers appears to be satisfactory to obtain the desirable results. In one embodiment, the layer had an exposed surface area of approximately 8.5 square millimeters. Preferably, the substrate 15 of tip 12 has a porous surface structure, such that the iridium oxide coating assumes the lacework contour of the surface and promotes ingrowth of cardiac tissue to reduce abrasion of the adjacent tissue.

Stem 14 and substrate 15 may be formed integrally or separately (in the latter case, the two are then pressed together and bonded) by conventional powder metallurgy process, in which powdered titanium is packed into a mold, compressed, and thereafter sintered at a temperature and for a time sufficient to cause partial melting into a relatively porous electrically conductive structure.

An exemplary preferred process for forming a TIROF film on porous titanium tip electrode substrates is as follows. The electrode tips are etched in hot 10% oxalic acid, 100° C. for 30 minutes; thereafter rinsed in distilled water and placed in an iridium solution with only the tip portions to be coated contacted by the solution. The Ir solution is prepared by dissolving 0.4 gram $IrCl_3 \cdot 3H_2O$ in 10 ml 20% HCl, heating the solution to evaporate the HCl down to one-quarter volume and restoring the original volume with absolute isopropanol, the resulting solution to be used within 7 to 14 days. Following a 16 hour soak in this solution, the electrodes are dried at room temperature for one hour, and then annealed at 320° C. for another hour. The steps of soaking, drying and annealing are repeated, and the electrodes are then annealed again at 320° C. for a period of from 3 to 6 hours.

In an exemplary SIROF process, the electrode substrate may be reactively coated with iridium oxide in a conventional diode RF sputtering system. The substrate is initially positioned and maintained in good thermal contact with the water cooled platform of the sputtering system. Any portion of the surface which is not to be coated is suitably masked. Pre-sputtering is performed with an iridium target in pure oxygen at an ambient pressure of about 20 microns for approximately 20 minutes to one-half hour. The pressure is then reduced to the range from about 2 to 4 microns, and sputtering is performed with a target power density of about 0.6 to 0.8 watt per square centimeter. The process is continued until an iridium oxide layer of the desired thickness is deposited.

For bipolar stimulation, the electrode assembly includes an anodic electrode 27, preferably of titanium, configured as a ring electrode insulatively spaced behind tip 12 by a sufficient distance to avoid the shunting of current between the edges of the two electrodes. The anode also may be coated with a layer 28 of iridium oxide at its exposed surface, in the same manner as cathodic electrode tip 12. A second coil 31 of conductive wire is maintained in electrical connection with the interior of anode 27 by confining the coil, for example, between the anode and a metal ring (not shown) at the far end of the anode. Coil 31 is part of the lead assembly, and is arranged via a connector (not shown) at the proximal end for coupling the anode to a point of reference potential at the pulse generator. An electrically insulating mass 30 of silicone rubber may be used to encapsulate the internal elements of the electrode assembly, including polyurethane sleeves 32 and 33, and an outer polyurethane sleeve 34 covers the assembly from cathode tip 12 to anode 27 leaving the IrO surfaces of those two electrodes exposed.

Referring now to FIG. 2, a pacing lead assembly 35 includes electrode assembly 10 at its distal end and is connected at its proximal end to appropriate points of electrical potential of the conventional circuitry, including the pulse generator, housed within a metallic case 38. The combination of the circuitry in case 38 and the pacing lead assembly 35 constitutes cardiac pacemaker 40. As shown in FIG. 2, the pacing lead assembly 35 is inserted transvenously until the iridium oxide coated cathodic tip is properly positioned in contact with or adjacent to excitable tissue within the selected chamber; in this example, the right ventricle 43 of the patient's heart 45. Case 28 houses a pulse generator, a detection circuit, the batteries, and other conventional electronic circuitry, and includes an electrical connector mating with the connector at the proximal end of the pacing lead assembly. In practice, the case is implanted in a surgical incision which forms a subcutaneous pouch in the patient's chest, after connection to the lead assembly.

The pacing lead assembly 35 shown in FIG. 2 may be arranged for unipolar stimulation, with the case 38 or a limited region 48 thereof comprising an iridium oxide-coated foil being used as the anode. Of course, in that situation the anodic ring and associated coil of the electrode assembly shown in FIG. 1 would not be present. Region 48 may include a substrate of iridium foil which has been anodized to form an AIROF film thereon, and the uncoated side of the foil then conductively bonded to titanium case 38. Alternatively, region 48 may comprise a titanium or iridium button on which an iridium oxide layer, preferably having a thickness exceeding 100 nanometers, is formed by the preferred process described earlier herein.

In operation of the pacemaker of FIG. 2, stimulating pulses delivered by the pulse generator to the cathodic electrode cause an electric field to be impressed on the myocardial tissue at the cathode site. If the field strength and current density of the electric field is sufficient to reach or exceed the stimulation threshold, capture is achieved. The efficient transduction of the iridium oxide layer on the cathode tip results in considerably lower stimulation thresholds and electrode polarization than may be achieved with pacing electrodes composed of materials heretofore utilized for such applications. Acute stimulation thresholds as low as approximately 0.2 volt have been observed in pacing experiments on test dogs using lead assemblies with iridium oxide coated cathodes.

A stimulating pulse is delivered by the pulse generator to the heart through the circuit which includes the lead, the cathodic electrode, the anodic electrode, the body tissue and fluid. The events leading up to the pacing depend upon the particular type of pacemaker, but in general the pulse is of relatively short duration, e.g., 0.5 ms, for the period of closure of a switch (typically, an NMOS FET) to discharge the main capacitor through a smaller coupling capacitor. The latter is charged in the process, and it is customary to actively discharge the coupling capacitor when the aforementioned switch is opened, by closing another switch (typically, a PMOS FET) to provide a reverse current path for an interval of about 10 ms. The sense amplifier is unhooked during stimulation and throughout the active discharge interval, but therefter receives signals representing electrical activity sensed by the tip electrode (cathode). With conventional pacing electrodes, electrode polarization may result in a lingering after-potential following delivery of each pacing pulse. The after-potential may continue for hundreds of milliseconds, and, if it extends beyond the refractory period, may easily result in false detection as a cardiac event. In contrast, the low polarization iridium oxide coated pacing electrodes of the present invention virtually eliminate after-potentials, and thereby allow sensing of evoked potentials and other valid cardiac events within a relatively short time after stimulation, approximately 25 ms and consistently within the first 100 milliseconds.

Figure 3:
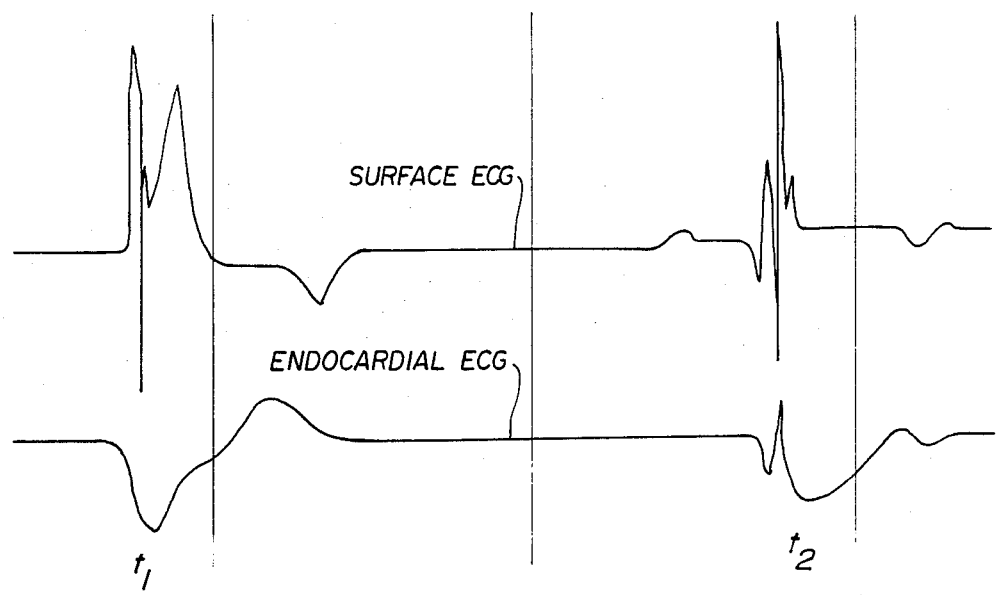
FIGS. 3 and 4 are electrograms taken from test dogs, respectively using conventional electrodes and iridium oxide coated electrodes for stimulation and sensing, in which the top portion of each FIG. represents a surface electrogram and the bottom portion an electrogram taken between the indifferent electrode and the tip electrode of an implanted lead assembly.
Figure 4:
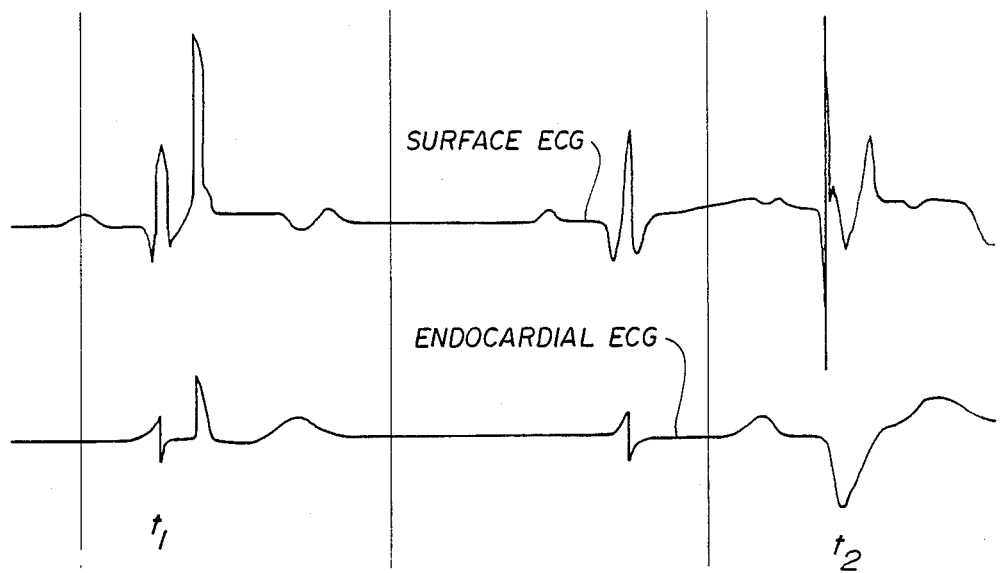

Referring now to FIGS. 3 and 4, each of these FIGS. shows an upper trace of a surface ECG, and a lower trace of an endocardial ECG taken across the the indifferent electrode and the stimulating cathodic electrode. The cathode was used for stimulation, and for sensing after the application of stimuli and at all other times. The traces in FIG. 3 were obtained from a test dog in which a lead assembly with a conventional platinum-iridium stimulating electrode was implanted. It will be observed that in the lower trace the two waveforms are confusingly similar, and indeed, appear to indicate capture at both times $t_1$ and $t_2$. However, the surface electrogram of the upper trace clearly indicates a pace with captured QRS at time $t_1$, and a P-wave and QRS complex with a pacing pulse at time $t_2$ but at that point the tissue is depolarized so there is no capture. In the latter instance it was the after-potential on the electrode that was detected. Although the traces of FIG. 3 visually allow the trained observer to distinguish between capture and noncapture, the distinction is not readily detected by conventional electronic circuitry. For example, the waveform at time $t_2$ in the lower trace of FIG. 3 would be detected as capture by a typical level detector.

Referring now to FIG. 4, these traces were obtained from a test dog in which the implanted lead assembly was provided with an iridium oxide coated stimulating electrode. It will be observed here that the lower trace indicates non-capture at time $t_1$ and capture at time $t_2$, and that the two are clearly distinguishable by detection circuitry as well.

It will be apparent from the foregoing description that variations are possible without departing from the inventive principles, e.g., use in defibrillation. Accordingly, the invention is to be limited only by the appended claims.

I claim:

1. A lead assembly for use in sensing capture of the heart in conjunction with pacing of the heart, comprising
    an electrode having a coating of iridium oxide on a surface thereof adapted to be in electrically coupled relationship with the heart when said lead assembly is implanted in a patient, to provide low polarization whereby the electrode is capable of sensing the evoked potential indicative of capture immediately after the heart is paced, and
    electrical conductor means connected to said electrode for electrically coupling said electrode to detecting circuitry of a cardiac pacemaker.
2. The lead assembly of claim 1, in which the iridium oxide coated surface is porous, and said coating follows the interstices of the porous surface.
3. The lead assembly of claim 1, in which said iridium oxide coating has a thickness exceeding 100 nanometers.
4. The lead assembly of claim 1, further including
    a second electrode having an iridium oxide coating on a surface thereof and insulatively spaced from the first-named electrode, and
    a second electrical conductor means connected to said second electrode for electrically coupling said second electrode to the circuitry of said cardiac pacemaker.
5. A cardiac pacemaker for stimulating and sensing electrical activity of a human heart, comprising
    a pulse generator means,
    a detection circuit means,
    means for supplying electrical power to said pulse generator means and said detection circuit means,
    an electrode means having a surface layer of iridium oxide to electrically interact with excitable cardiac tissue of said heart when a stimulating pulse is applied thereto and for rapid recovery from after-potentials at said surface layer upon cessation of the stimulating pulse to enable sensing of the potential evoked and verification of capture of the heart by said stimulating pulse, and
    a conductor means having a distal end and a proximal end, said distal end electrically connected to said electrode means and said proximal end electrically connected to said pulse generator means and said detection circuit means, for applying stimulating pulses from said generator means to said electrode means and applying evoked potentials sensed by said electrode means to said detection circuit means.
6. The cardiac pacemaker of claim 5, further including a metal case housing said pulse generator means, detection circuit means, and power supply means, and
    an indifferent electrode means affixed to said case and having a surface layer of iridium oxide thereon, said indifferent electrode means connected to a point of reference potential of said power supply means to cooperate with the first-named electrode means for unipolar stimulation of the heart.
7. A method of artificially pacing a heart and detecting capture thereof, comprising the steps of
    introducing an electrode having an iridium oxide surface layer thereon into cardiac tissue stimulating relationship with the heart,
    impressing electrical stimuli on said electrode at a rate within the range selected to provide the desired stimulation of the heart, and
    detecting the electrical activity of the heart sensed at the surface of said iridium oxide layer within less than 100 milliseconds after a stimulus to determine whether the heart is captured by said stimulus.
8. The method according to claim 7, wherein
    said electrode is introduced transvenously into a selected chamber of the heart to position said electrode with said iridium oxide layer in cardiac tissue stimulating relationship with the endocardium of said chamber.
9. An implantable lead assembly for electrical conduction between an electrical energy processing means and the myocardium of a human heart, said lead assembly comprising low polarization electrode means having a size and shape configured to be positioned in proximity to the myocardium for impressing electrical stimuli thereon and, abruptly at the completion of a stimulus, for sensing whether the heart is captured by said stimulus by detecting the evoked potential indicative of capture, said electrode means having an iridium oxide coating on at least a portion of the surface thereof adapted to be in close proximity to the myocardium, and conductor means for electrically interconnecting said energy processing means and said electrode means to conduct said electrical stimuli and said detected evoked potential therebetween.

10. The lead assembly of claim 9, wherein said iridium oxide coating has a thickness of at least 100 nanometers.

* * * * *